United States Patent
Hao et al.

(10) Patent No.: US 11,110,042 B2
(45) Date of Patent: *Sep. 7, 2021

(54) METHODS FOR SYNTHESIZING STANNOUS PYROPHOSPHATE

(71) Applicant: Colgate-Palmolive Company, New York, NY (US)

(72) Inventors: Zhigang Hao, Bridgewater, NJ (US);
Paul Thomson, Piscataway, NJ (US);
Long Pan, Somerset, NJ (US); Tatiana Brinzari, Piscataway, NJ (US);
Guofeng Xu, Plainsboro, NJ (US);
Sergio Leite, Monmouth Junction, NJ (US); Yu Wang, Edison, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/820,909

(22) Filed: Mar. 17, 2020

(65) Prior Publication Data
US 2020/0330342 A1 Oct. 22, 2020

Related U.S. Application Data

(60) Provisional application No. 62/835,752, filed on Apr. 18, 2019.

(51) Int. Cl.
*A61K 8/24* (2006.01)
*A61Q 11/00* (2006.01)

(52) U.S. Cl.
CPC ............... *A61K 8/24* (2013.01); *A61Q 11/00* (2013.01); *A61K 2800/92* (2013.01)

(58) Field of Classification Search
None
See application file for complete search history.

(56) References Cited

U.S. PATENT DOCUMENTS

| 3,028,216 | A | 4/1962 | Gemmell et al. |
| 6,350,436 | B1 | 2/2002 | Glandorf et al. |
| 2018/0168956 | A1 | 6/2018 | Rege et al. |
| 2018/0168957 | A1 | 6/2018 | Rege et al. |

FOREIGN PATENT DOCUMENTS

| CA | 645784 | 7/1962 |
| CN | 102951626 | 3/2013 |
| GB | 1565865 | 4/1980 |
| WO | 2017/117363 | 7/2017 |

OTHER PUBLICATIONS

International Search Report and the Written Opinion of the International Searching Authority issued in International Application PCT/US2020/023068 dated Jun. 5, 2020.
CN102951626, Guangxi University of Technology, "Method for Preparing High-Purity Stannous Pyrophosphate," Mar. 6, 2013, English language machine translation of abstract, Espacenet, date obtained: Oct. 1, 2020, 1 page <https://worldwide.espacenet.com/patent/search/family/047761094/publication/CN102951626A?q=CN102951626>.

*Primary Examiner* — Brian J Davis

(57) ABSTRACT

Disclosed herein are improved methods for the synthesis of stannous pyrophosphate, as well as improved methods for the manufacture of oral care compositions comprising stannous pyrophosphate.

20 Claims, 3 Drawing Sheets

METHODS FOR SYNTHESIZING STANNOUS PYROPHOSPHATE

CROSS-REFERENCE TO RELATED APPLICATIONS

This application is a United States application filed under 35 U.S.C. § 111(a) claiming priority to and the benefit of U.S. Provisional Application No. 62/835,752, filed on Apr. 18, 2019, the contents of which are hereby incorporated by reference in its entirety.

BACKGROUND

Oral cavity bacteria are the primary cause of dental ailments, including caries, gingivitis, periodontitis, and halitosis. Dental erosion involves demineralization and damage to the tooth structure due to acid attack from nonbacterial sources. Erosion is found initially in the enamel and, if unchecked, may proceed to the underlying dentin. Dental erosion may be caused or exacerbated by acidic foods and drinks, exposure to chlorinated swimming pool water, and regurgitation of gastric acids. Dental plaque is a sticky biofilm or mass of bacteria that is commonly found between the teeth, along the gum line, and below the gum line margins. Dental plaque can give rise to dental caries and periodontal problems such as gingivitis and periodontitis. Dental caries tooth decay or tooth demineralization caused by acid produced from the bacterial degradation of fermentable sugar.

Oral care compositions which contain stannous ion sources exhibit excellent clinical benefits, particularly in the reduction of gingivitis and in the treatment or prevention of erosive tooth demineralization. Stannous fluoride is well known for use in clinical dentistry with a history of therapeutic benefits over forty years. However, until recently, its popularity has been limited by its instability in aqueous solutions. The instability of stannous fluoride in water is primarily due to the reactivity of the stannous ion ($Sn^{2+}$). Stannous salts readily hydrolyze at a pH above 4, resulting in precipitation from solution. It has traditionally been thought that this formation of insoluble stannous salts results in a loss of therapeutic properties.

Soluble metal ions, such as stannous, may also react unfavorably polymeric rheological modifiers, such as modified celluloses (e.g., carboxymethyl cellulose) and gums (e.g., xanthan gum or carrageenan gum). Such compounds often considered to be incompatible with divalent metal ions.

Recently there has been a renewed interest in using insoluble stannous salts in oral care compositions as a way of overcoming these issues. One leading contender is stannous pyrophosphate, an agent which has been known since at least the 1960's as a dentifrice polishing agent. Stannous pyrophosphate (also known as SnPP) has the formula $Sn_2P_2O_7$, and it combines the tetravalent pyrophosphate anion with divalent Sn(II) cation. It is substantially insoluble in water, especially at an acidic pH.

The use of stannous pyrophosphate in making oral care products has been limited by its high cost. Stannous pyrophosphate is significantly more expensive to purchase on the global chemical market than other more common stannous compounds, such as stannous chloride and stannous fluoride. Therefore, oral care products can be manufactured much more cost effectively if a low-cost stannous salt, such as stannous chloride, is purchased as a material from which stannous pyrophosphate can be made.

Various methods of synthesizing stannous pyrophosphate have been known in the art. For example, Gemmell et al. synthesize SnPP by reacting an aqueous slurry or solution of stannous chloride with sodium acid pyrophosphate (disodium pyrophosphate) followed by neutralization with excess base (such as sodium hydroxide or sodium carbonate). See U.S. Pat. No. 3,028,216. One drawback of this is that the reaction results in a sodium chloride by-product which can be difficult to remove, hindering the production of highly pure stannous pyrophosphate. In some cases, this impurity can impart a highly undesirable salty taste to the product. This is especially true if this prior art method is adapted as an in-situ method of making stannous pyrophosphate during the manufacture of the oral care product itself.

There is thus still a need for additional methods which provide improved ease, efficiency and/or yield.

BRIEF SUMMARY

It has now been discovered that stannous pyrophosphate can be more efficiently prepared by reacting stannous chloride with tetrasodium pyrophosphate (TSPP) in a water or water/alcohol mixture, followed by precipitation, filtration and freeze-drying, to obtain highly pure product without by-products causing off-flavors. In addition, it has been further discovered that an oral care composition comprising stannous pyrophosphate can be more effectively prepared by reacting stannous chloride with tetrasodium pyrophosphate in a water or water/alcohol mixture, optionally followed by precipitation, filtration and resuspension, at the point of manufacture of the oral care composition. The latter "in-situ" method provides improved economies of manufacture by reducing costs associated with transport, storage, and purification of the stannous pyrophosphate material made from the stannous chloride.

The invention further provides oral care compositions, for example mouthwash, oral gel or dentifrice compositions, that comprise the stannous pyrophosphate made according to the present synthetic methods.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

Figure 1:
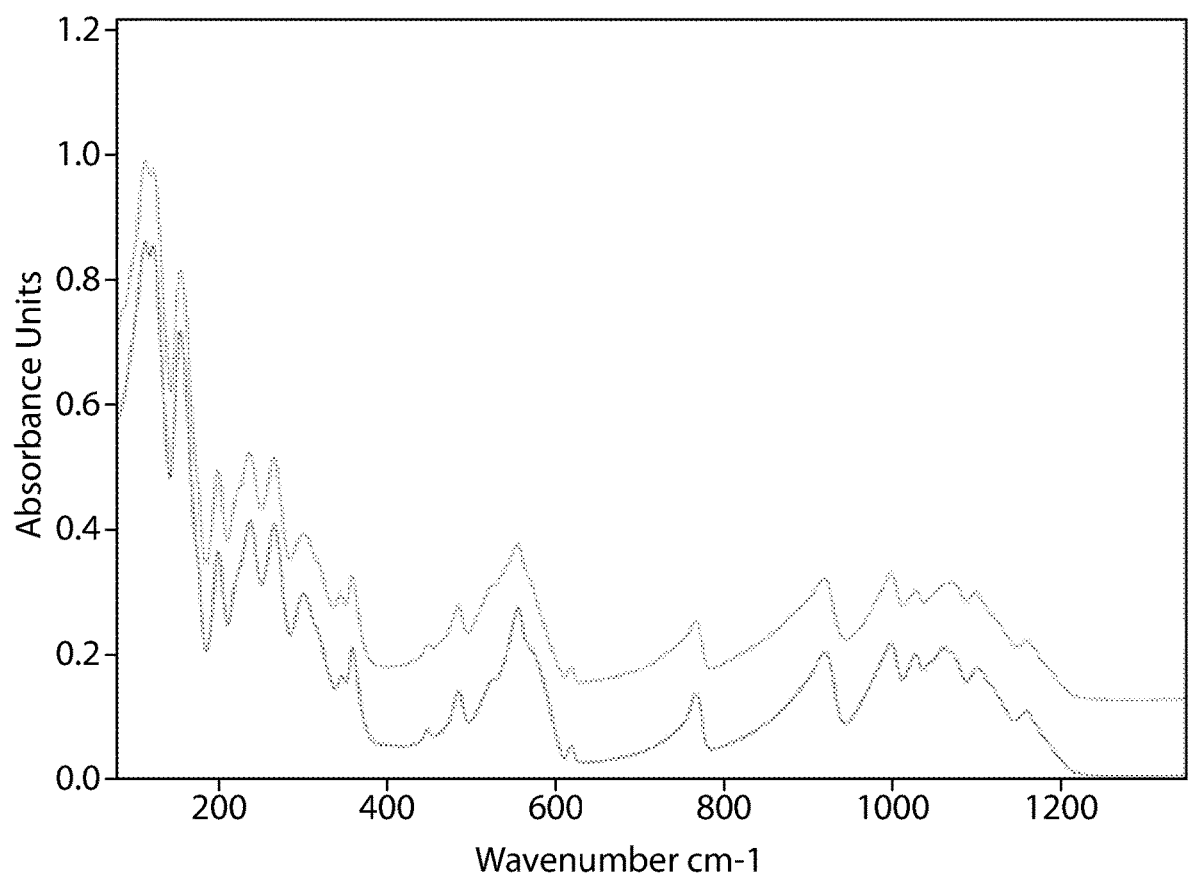
FIG. 1 shows overlaid Fourier-transform infrared (FTIR) spectra comparing the SnPP product made according to the present disclosure, by reacting stannous chloride and tetrasodium pyrophosphate (TSPP) in water for 30 minutes, followed by precipitation, filtration and freeze-drying (top spectrum) compared to reference SnPP purchased from a global chemical supplier (bottom spectrum). The spectra are offset for clarity.

The following description of the preferred embodiment(s) is merely exemplary in nature and is in no way intended to limit the invention, its application, or uses.

The invention therefore provides, in a first aspect, a method of making stannous pyrophosphate (Method 1), comprising the steps of (1) reacting stannous chloride with tetrasodium pyrophosphate in a water or water/alcohol solvent mixture, (2) precipitating the stannous pyrophosphate product, (3) recovering the stannous pyrophosphate product by filtration, and (4) freeze-drying the stannous pyrophosphate product. In further embodiments of Method 1, the present disclosure provides:

1.1. Method 1 wherein the stannous chloride is stannous chloride dihydrate ($SnCl_2$-$2H_2O$).
1.2. Method 1 or 1.1, wherein the tetrasodium pyrophosphate is the only pyrophosphate salt added to the reaction.
1.3. Method 1 or 1.1, wherein the stannous chloride and the tetrasodium pyrophosphate are combined in a molar ratio of 1:1 to 1:3, e.g., from 1:1 to 1:2 or from 1:1 to 1.5, or from 1:1 to 1.25, or about 1:1.
1.4. Method 1 or any of 1.1 et seq., wherein solvent for step (1) is water.
1.5. Method 1 or any of 1.1 et seq., wherein the solvent for step (1) is a water/alcohol mixture.
1.6. Method 1.5, wherein the alcohol is selected from methanol, ethanol, propanol, isopropanol, butanol, ethylene glycol, 1,2-propylene glycol, 1,3-propylene glycol, cyclopentane-1,2-diol, cyclohexane-1,2-diol, neopentyl glycol, glycerol, 1,2-butanediol, 1,3-butanediol, 1,4-butanediol, 1,5-pentanediol, pentaerythritol, and sorbitol.
1.7. Method 1.6, wherein the alcohol is selected from 1,2-propylene glycol, 1,3-propylene glycol, glycerol and sorbitol.
1.8. Method 1.5, 1.6 or 1.7, wherein the ratio of water to alcohol is 5:1 to 1:5 v/v, e.g., 4:1 to 1:4, 3:1 to 1:3, or 2:1 to 1:2.
1.9. Method 1 or any of 1.1 et seq., wherein step (1) takes place at 20° C. to 100° C., e.g., at 25° C. to 80° C., or at 35° C. to 70° C., or at 45° C. to 70° C., or at 55° C. to 70° C., or at about 65° C.
1.10. Method 1 or any of 1.1 et seq., wherein step (1) takes place at 20° C. to 35° C. or at 20° C. to 30° C.
1.11. Method 1 or any of 1.1 et seq., wherein the reaction mixture is allowed to cool between step (1) and step (2), e.g., to cool to room temperature (e.g., 20° C. to 30° C.
1.12. Method 1 or any of 1.1 et seq., wherein the precipitation of step (2) occurs unassisted, e.g., upon cooling of the reaction mixture from its reaction temperature.
1.13. Method 1 or any of 1.1 et seq., wherein the precipitation of step (2) is promoted by the addition of water to the reaction mixture of step (1), e.g., cold water (e.g., water at a temperature of 0° C. to 25° C.).
1.14. Method 1 or any of 1.1 et seq., wherein the filtered product from step (3) is washed one or more times with water before step (4).
1.15. Method 1.14, wherein the filtered product from step (3) is washed once, twice or three times with water before step (4).
1.16. Method 1 or any of 1.1 et seq., wherein the reaction step (1) is substantially complete (e.g., greater than 90% conversion) in 0-3 hours, e.g., in 0-2 hours or in 0-1 hour, or in 0-30 minutes, e.g., in 1-30 minutes, or 1-20 minutes, or 1-15 minutes or 1-10 minutes.
1.17. Method 1 or any of 1.1 et seq., wherein the method does not comprise the use or addition of any reactants, reagents or other chemicals other than the stannous chloride, the tetrasodium pyrophosphate, the water or water/alcohol solvent mixture, and optionally the washing water (e.g., the method does not comprise the addition of any base).
1.18. Method 1 or any of 1.1 et seq., wherein the method further comprises the step of isolating the stannous pyrophosphate product, and/or the step of packaging the stannous pyrophosphate product.
1.19. Stannous pyrophosphate made according to Method 1 or any of Methods 1.1 to 1.18.
1.20. An oral care composition comprising stannous pyrophosphate made according to Method 1 or any of 1.1 to 1.18.

In another aspect, the invention further provides a method of making an oral care composition comprising stannous pyrophosphate (Method 2), comprising the steps of (1) reacting stannous chloride with tetrasodium pyrophosphate in a water or water/alcohol solvent mixture in a reactor tank, (2) precipitating the stannous pyrophosphate product, optionally (3) recovering the stannous pyrophosphate product by filtration, optionally (4) freeze-drying the stannous pyrophosphate product, and (5) transferring the stannous pyrophosphate product into a mixing tank containing at least one oral care ingredient and at least one orally acceptable solvent.

In further embodiments of Method 2, the present disclosure provides:

2.1. Method 2, wherein the stannous chloride is stannous chloride dihydrate ($SnCl_2$-$2H_2O$).
2.2. Method 2 or 2.1, wherein the tetrasodium pyrophosphate is the only pyrophosphate salt used in the method.
2.3. Method 2 or 2.1, wherein the stannous chloride and the tetrasodium pyrophosphate are combined in a molar ratio of 1:1 to 1:3, e.g., from 1:1 to 1:2 or from 1:1 to 1.5, or from 1:1 to 1.25, or about 1:1.
2.4. Method 2 or any of 2.1 et seq., wherein solvent for step (1) is water.
2.5. Method 2 or any of 2.1 et seq., wherein the solvent for step (1) is a water/alcohol mixture.
2.6. Method 2.5, wherein the alcohol is selected from methanol, ethanol, propanol, isopropanol, butanol, ethylene glycol, 1,2-propylene glycol, 1,3-propylene glycol, cyclopentane-1,2-diol, cyclohexane-1,2-diol, neopentyl glycol, glycerol, 1,2-butanediol, 1,3-butanediol, 1,4-butanediol, 1,5-pentanediol, pentaerythritol, and sorbitol.
2.7. Method 2.6, wherein the alcohol is selected from 1,2-propylene glycol, 1,3-propylene glycol, glycerol and sorbitol.
2.8. Method 2.5, 2.6 or 2.7, wherein the ratio of water to alcohol is 5:1 to 1:5 v/v, e.g., 4:1 to 1:4, 3:1 to 1:3, or 2:1 to 1:2.
2.9. Method 2 or any of 2.1 et seq., wherein step (1) takes place at 20° C. to 100° C., e.g., at 25° C. to 80° C., or at 35° C. to 70° C., or at 45° C. to 70° C., or at 55° C. to 70° C., or at about 65° C.

2.10. Method 2 or any of 2.1 et seq., wherein step (1) takes place at 20° C. to 35° C. or at 20° C. to 30° C.

2.11. Method 2 or any of 2.1 et seq., wherein the reaction mixture is allowed to cool between step (1) and step (2), e.g., to cool to room temperature (e.g., 20° C. to 30 C.

2.12. Method 2 or any of 2.1 et seq., wherein the precipitation of step (2) occurs unassisted, e.g., upon cooling of the reaction mixture from its reaction temperature.

2.13. Method 2 or any of 2.1 et seq., wherein the precipitation of step (2) is promoted by the addition of water to the reaction mixture of step (1), e.g., cold water (e.g., water at a temperature of 0° C. to 25° C.).

2.14. Method 2 or any of 2.1 et seq., wherein the step (3) and step (4) are omitted, and step (2) yields a liquid slurry of the stannous pyrophosphate product precipitate in the water or water/alcohol solvent mixture and this slurry is transferred into the mixing tank of step (5).

2.15. Method 2 or any of 2.1 et seq., wherein step (4) is omitted, and the filtered solid from step (3) is transferred into the mixing tank of step (5).

2.16. Method 2.15, wherein the filtered product from step (3) is washed one or more times with water before being transferred into the mixing tank of step (5).

2.17. Method 2.16, wherein the filtered product from step (3) is washed once, twice or three times with water before being transferred into the mixing tank of step (5).

2.18. Method 2.15, 2.16, or 2.17, wherein the filtered solid from step (3), optionally after washing with water, is resuspended in an orally acceptable liquid and the resulting suspension is transferred into the mixing tank of step (5).

2.19. Method 2.18, wherein the orally acceptable liquid is selected from water, glycerol, propylene glycol, sorbitol or a mixture thereof.

2.20. Method 2 or any of 2.1 et seq., wherein the reaction step (1) is substantially complete (e.g., greater than 90% conversion) in 0-3 hours, e.g., in 0-2 hours or in 0-1 hour, or in 0-30 minutes, e.g., in 1-30 minutes, or 1-20 minutes, or 1-15 minutes or 1-10 minutes.

2.21. Method 2 or any of 2.1 et seq., wherein method steps (1)-(5) do not comprise the use or addition of any reactants, reagents or other chemicals other than the stannous chloride, the tetrasodium pyrophosphate, the water or water/alcohol solvent mixture, the optional washing water and the optional orally acceptable liquid for resuspension of the filtered precipitate (e.g., the method does not comprise the addition of any base).

2.22. Method 2 or any of 2.1 et seq., wherein the method further comprises the step of incorporating stannous fluoride into the oral care composition.

2.23. An oral care composition made according to Method 2 or any of 2.1 to 2.22.

In a third aspect, the present disclosure provides an oral care composition (Composition 3) comprising stannous pyrophosphate and sodium chloride in a molar ratio of about 4 parts sodium chloride to one part stannous pyrophosphate. In further embodiments of this aspect, the present disclosure provides:

3.1 Composition 3, wherein the composition comprises sodium chloride and stannous pyrophosphate in a molar ratio of about 3:1 to about 4:1, e.g., about 3.5:1 to about 4:1.

3.2 Composition 3 or 3.1, wherein the composition comprises from 0.1 to 3% by weight of stannous pyrophosphate, e.g., from 0.5 to 2% by weight, or about 1% by weight.

3.3 Composition 3 or any of 3.1 et seq., wherein the composition comprises 0.05 to 2% by weight of sodium chloride, e.g., from 0.1 to 1.0% by weight, or about 0.5% by weight.

3.4 Composition 3 or any of 3.1 et seq., wherein the composition further comprises stannous fluoride, e.g., in an amount of 0.1 to 1.0 wt %, or about 0.45 wt %.

3.5 Composition 3 or any of 3.1 et seq., wherein the composition further comprises zinc citrate, zinc oxide or a combination thereof.

3.6 Composition 3.5, wherein the composition comprises from 0.1 to 1.0% by weight of zinc citrate (e.g., zinc citrate trihydrate), from 0.5 to 2.0% by weight of zinc oxide, or a combination thereof 3.7 Composition 3.6, wherein the composition comprises about 0.5% by weight of zinc citrate (e.g., zinc citrate trihydrate), about 1.0% zinc oxide, or a combination thereof.

3.8 Composition 3 or any of 3.1 et seq., wherein the composition further comprises one or more humectants, e.g., selected from glycerol, sorbitol, propylene glycol, and xylitol.

3.9 Composition 3 or any of 3.1 et seq., wherein the composition further comprises one or more abrasives (e.g., silica), anionic surfactants (e.g., sodium lauryl sulfate), zwitterionic surfactants (e.g., cocamidopropyl betaine), gums or polymers (e.g., methyl vinyl ether/maleic anhydride copolymer, sodium carboxymethyl cellulose, polyvinyl pyrrolidone, polyethylene glycol, cellulose, hydroxyethyl cellulose).

3.10 Composition 3 or any of 3.1 et seq., wherein the sodium chloride and stannous pyrophosphate are made by reacting stannous chloride and tetrasodium pyrophosphate.

3.11 Composition 3 or any of 3.1 et seq., wherein the composition further comprises tetrasodium pyrophosphate (e.g., as an anti-calculus agent, in addition to any tetrasodium pyrophosphate used to make the stannous pyrophosphate), e.g., from 1 to 5% by weight of tetrasodium pyrophosphate, or from 2 to 4%, or 2 to 3% or about 2%.

Unless stated otherwise, all percentages of composition components given in this specification are by weight based on a total composition or formulation weight of 100%.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the invention extends to the product of the combination of the listed ingredients.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should

EXAMPLES

Example 1: Synthesis of SnPP Using TSPP

Synthesis:

400 mL water is heated to 60° C. in a 1000 mL glass beaker. 21.26 g of tetrasodium pyrophosphate (TSPP) is completely dissolved in the water with a continuous blender stirring at 500 rpm. Then, 36.10 g of $SnCl_2.2H_2O$ is added into the solution with stirring, and the reaction mixture is maintained at the same temperature for 30 minutes. A precipitate is observed to begin forming quickly. After 30 minutes, the reaction mixture is cooled down to room temperature. The majority of the supernatant is decanted and removed. The residual material, including the precipitate and remaining supernatant, are transferred into several 50 mL centrifuge tubes. The tubes are centrifuged at a speed of 8500 rpm for 10 minutes to pellet the precipitate, and the supernatant is then removed from each tube. In each tube, the pelleted precipitate is re-suspended with about 5 volumes of water, the suspension is vortexed for one minute, then the tubes are centrifuged again. This washing procedure is repeated two additional times. After removing the last of the supernatant from each tube are put into a dry ice/acetone cooling bath. After the water residues appear to be frozen, the centrifuge tubes are transferred into a freeze dry machine for over 24 hours to remove the last traces of water. The dried samples are used for calculation of reaction yield, iodine titration, FTIR and PXRD characterization and stannous pyrophosphate from Sigma was used as the reference materials.

31.69 grams of stannous pyrophosphate product is collected after freeze-drying, for a yield of 96.3%. Analysis confirms the identity of the product as stannous pyrophosphate, as described below.

The same reaction procedure was also repeated three times with the reaction time set to 10 minutes, 20 minutes, or 30 minutes. At the conclusion of the stated time period, the reaction was cooled to room temperature, washed and dried as described above.

FTIR Experiments:

Infrared spectra are collected using a Bruker Vertex 70 FTIR spectrometer equipped with a GladiATR diamond ATR accessory (Pike technologies, Madison, Wis.). The spectral range is 80-4000 $cm^{-1}$ and a resolution of 4 $cm^{-1}$ is used. All measurements are carried out at room temperature.

Stannous pyrophosphate reference samples are purchased from Sigma. The comparative FTIR spectra are shown in FIG. 1. The data demonstrates that the product obtained matches the spectrum for known stannous pyrophosphate material.

Figure 2:
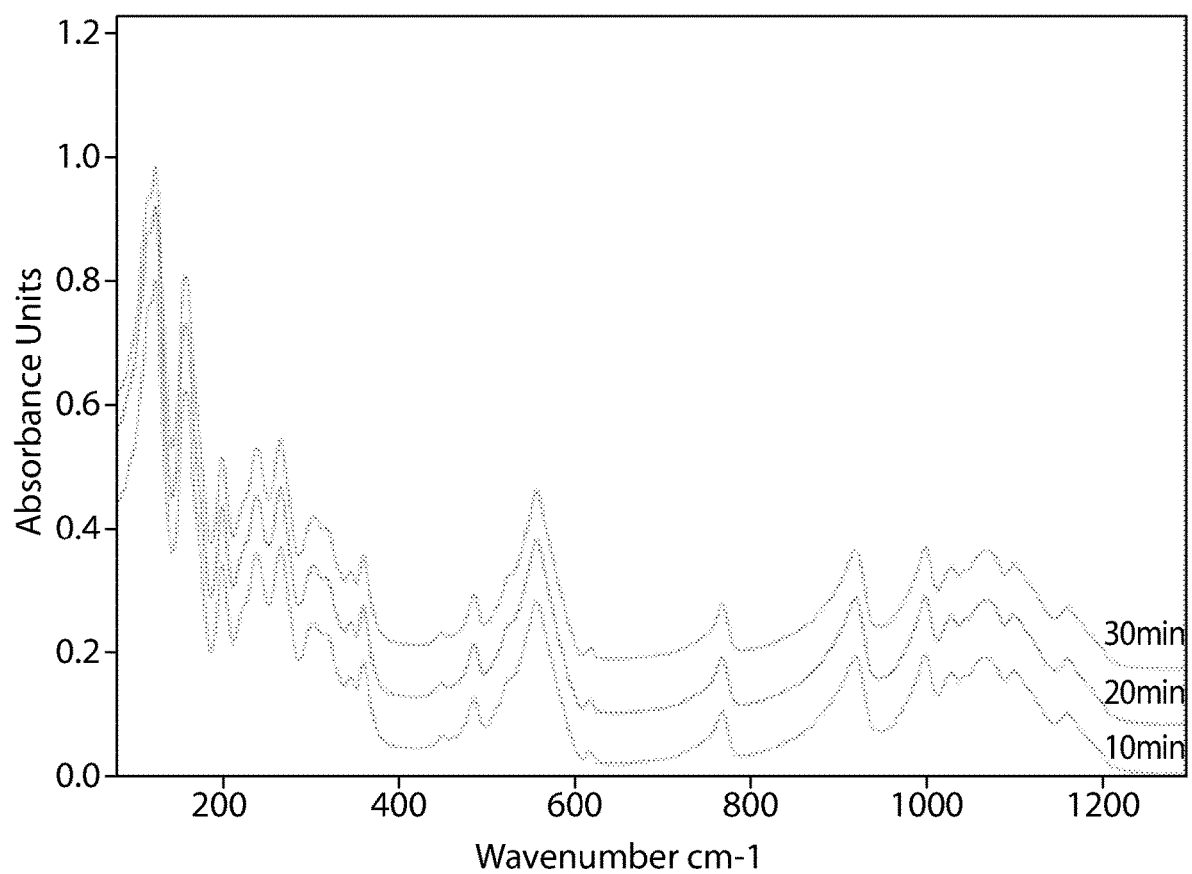
FIG. 2 shows overlaid Fourier-transform infrared (FTIR) spectra comparing the SnPP product made according to the present disclosure, by reacting stannous chloride and tetrasodium pyrophosphate (TSPP) in water, followed by precipitation, filtration and freeze-drying, wherein the reaction is conducted for 10 minutes (bottom), 20 minutes (middle), or 30 minutes (top). The spectra are offset for clarity.

The products obtained after stopping the reaction after 10, 20 and 30 minutes are also compared by FTIR, as shown in FIG. 2. The results show that the products are substantially identical in their FTIR spectra. This demonstrates that the synthetic reaction is finished within 10 minutes.

PXRD experiments: Powder X-Ray Diffraction (PXRD) of the freeze-dried product is carried out using a Rigaku D/M-2200T automated diffraction system with Cu Kα irradiation (k=1.5406 Å). The goniometer is configured in a step-scan mode with 5 s scans during each 0.02° step over a range from θ=5° to θ=50°.

Figure 3:
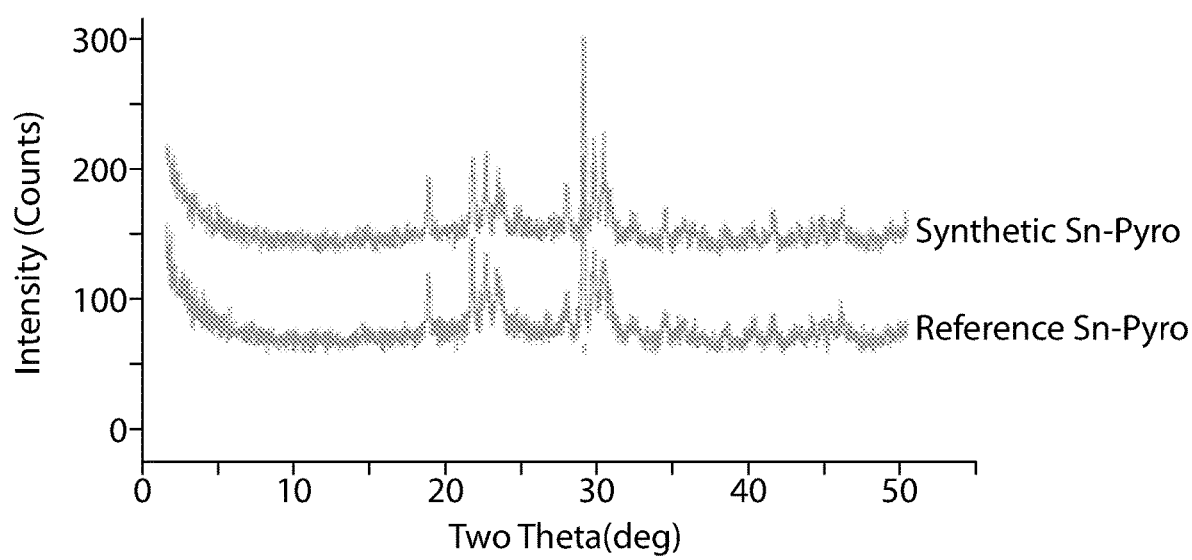
FIG. 3 shows overlaid powder X-ray diffraction (PXRD) spectra comparing the SnPP product made according to the present disclosure, by reacting stannous chloride and tetrasodium pyrophosphate (TSPP) in water for 30 minutes, followed by precipitation, filtration and freeze-drying (top spectrum) compared to reference SnPP purchased from a global chemical supplier (bottom spectrum).

The same stannous pyrophosphate reference sample as above is used. The results are shown in FIG. 3. No significant difference is found between the two materials, which further confirms the identity of the product as stannous pyrophosphate.

Iodine Titration:

50 mg of the dried stannous pyrophosphate product is transferred into a 120 mL jar with 60 mL of water. The powder is mixed and suspended using a magnetic stir bar. 1 mL of concentrated HCl (35%) solution is added to dissolve the suspended material. 0.1N iodine solution is used to titrate the stannous ion present. The titration reaction is: $Sn_2P_2O_7+2I_2 \rightarrow SnP_2O_7+SnI_4$.

The titration is found to require 4.5 mL of 0.1N iodine solution (0.45 mM Iodine), which indicates that the 50 mg sample of product contains 0.027 g of stannous (I), or, 94% of the theoretical amount. This shows that the product is approximately 94% pure.

Example 2: Stability of Stannous Pyrophosphate of Example 1

1 gram of stannous pyrophosphate obtained from Example 1 is mixed with 0.454 gram of $SnF_2$ in either water, water-glycerin or water-sorbitol mixtures. As a control, 1 gram of stannous chloride is also mixed with 0.454 grams of SnF2 in water, water-glycerin or water-sorbitol. The pH of each mixture is adjusted to about 7 with magnetic stirring. Each mixture is aged at to 60° C. for two weeks. The appearance of the mixture is recorded, and soluble stannous and fluoride contents are analyzed.

No significant changes in color are observed for either of the three solvent systems for the stannous pyrophosphate/stannous fluoride mixture. Each mixture shows a white solid suspended in a colorless solution. In contrast, in the water and water-glycerin solvent systems, the stannous chloride/stannous fluoride mixture changes to a gray color. Stannous and fluoride ion analysis show that in all three solvent systems for the stannous pyrophosphate/stannous fluoride combination, the soluble stannous fluoride content is stable at 60° C. through the end of the 2-week aging period. In contrast, the soluble stannous fluoride concentration dropped significantly for the stannous chloride/stannous fluoride mixture in each solvent system.

Example 3: In-situ Batch Formulation of Stannous Pyrophosphate for Toothpaste Composition A process development scale plant process is evaluated for the manufacture of a lot of toothpaste. Toothpaste 1 is formulated from the components shown in the table below:

| Ingredient | Wt. % |
| --- | --- |
| Stannous Fluoride | 0.45 |
| Stannous Chloride dihydrate | 1.1% |
| Tetrasodium pyrophosphate | 2.6% |
| Zinc Citrate trihydrate | 0.5% |
| Zinc Oxide | 1.0% |
| Glycerin | 42.4% |
| Propylene Glycol | 4.0% |
| Water (Q.S.) | ~8.8% |
| Polyethylene Glycol 600 | 3.0% |
| Gums, Anionic and Neutral Polymers | 2.85% |
| Methyl vinyl ether/maleic acid copolymer | 0.6% |
| Anionic Surfactant | 1.75% |
| Zwitterionic Surfactant | 1.0% |
| Silicas | 24% |

-continued

| Ingredient | Wt. % |
|---|---|
| Flavors, Colors, Sweeteners | 2.25% |
| Buffer/pH agents | 3.65% |

In a first pre-mix tank A, water (4.5% of final formulation), buffers and sweetener are combined and stirred together. In a second pre-mix tank B, glycerin (7.0% of final formulation) and tetrasodium pyrophosphate (2.0 wt % of final formulation) are combined and stirred together. In a third pre-mix tank C, glycerin (10% of final formulation), polyethylene glycol, propylene glycol, and gums, anionic and neutral polymers are combined and stirred together. In a fourth pre-mix tank D, water (4.3% of final formulation) is heated to 60° C., and tetrasodium pyrophosphate (0.64% of final formulation) is added to form a homogenous solution. The stannous chloride dihydrate is then added and the mixture is stirred for 15 minutes at 60° C., then the mixture is cooled to room temperature. A precipitate of stannous pyrophosphate is observed to form. To a primary mixing tank is added the contents of pre-mix Tank C followed by the remaining content of glycerin (25.4% of final formulation), followed by the contents of pre-mix Tank C. The mixing tank is stirred for ten minutes, then is heated to 80° C., and maintained for 30 minutes, then cooled. The contents of pre-mix tank D are then added followed by stirring for 5 minutes. The contents of pre-mix tank B, zinc oxide, zinc citrate, methyl vinyl ether copolymer, and remaining buffer/pH agents are added. After additional mixing, the remaining components of the composition, silicas, colors, flavors, zwitterionic surfactant, and anionic surfactant, are added to yield a gel.

For comparison, Toothpaste 2 is also prepared according to the same composition table and procedure as outline for Toothpaste 1, except for the following: (1) the toothpaste is prepared using 1.0 wt % stannous pyrophosphate (commercial) and 2.0% tetrasodium pyrophosphate, with no stannous chloride dihydrate; (2) pre-mix B contains the 2.0% tetrasodium pyrophosphate, the 1.0% stannous pyrophosphate and glycerin (10% of final formulation); (3) pre-mix C contains glycerin in an amount of 7% of the final formulation instead of 10%; (4) pre-mix D contains water (4.5% of final formulation) and the anionic surfactant; (5) the contents of pre-mix tank D is added to the end, after silicas, colors, flavors and zwitterionic surfactant.

Toothpaste 1 and Toothpaste 2 are compared in a 13-week accelerated aging study conducted at 40° C. Soluble zinc, soluble tin and ionic fluoride are measured. The results are shown in the table below:

|  | Total Zinc (%) | Soluble Zinc (%) | Total Tin (%) | Soluble Tin (%) | Ionic Fluoride (ppm) |
|---|---|---|---|---|---|
| Toothpaste 1 | | | | | |
| Initial | 0.96 | 0.62 | 0.85 | 0.81 | 1133 |
| 4 weeks | — | 0.67 | — | 0.6 | 906 |
| 8 weeks | — | 0.65 | — | 0.44 | 869 |
| 13 weeks | — | 0.56 | — | 0.71 | 813 |
| Toothpaste 2 | | | | | |
| Initial | 0.98 | 0.58 | 0.89 | 0.80 | 1081 |
| 4 weeks | — | 0.62 | — | 0.54 | 944 |
| 8 weeks | — | 0.51 | — | 0.55 | 834 |
| 13 weeks | — | 0.53 | — | 0.67 | 750 |

The results show that similar zinc, tin and fluoride stability is obtained when the composition is manufactured using the in-situ stannous pyrophosphate method as compared to using commercial stannous pyrophosphate as an ingredient.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the scope of the invention should be construed broadly as set forth in the appended claims.

The invention claimed is:

1. A method of making an oral care composition comprising stannous pyrophosphate, comprising the steps of (1) reacting stannous chloride with a tetrasodium pyrophosphate (TSPP) in a water or water/alcohol solvent mixture in a reactor tank, (2) precipitating the stannous pyrophosphate product, optionally (3) recovering the stannous pyrophosphate product by filtration, optionally (4) freeze-drying the stannous pyrophosphate product, and (5) transferring the stannous pyrophosphate product into a mixing tank containing at least one oral care ingredient and at least one orally acceptable solvent.

2. The method according to claim 1, wherein the stannous chloride is stannous chloride dihydrate ($SnCl_2 \cdot 2H_2O$).

3. The method according to claim 1, wherein the stannous chloride and the tetrasodium pyrophosphate are combined in a molar ratio of 1:1 to 1:3.

4. The method according to claim 1, wherein solvent for step (1) is water.

5. The method according to claim 1, wherein the solvent for step (1) is a water/alcohol mixture.

6. The method according to claim 5, wherein the alcohol is selected from methanol, ethanol, propanol, isopropanol, butanol, ethylene glycol, 1,2-propylene glycol, 1,3-propylene glycol, cyclopentane-1,2-diol, cyclohexane-1,2-diol, neopentyl glycol, glycerol, 1,2-butanediol, 1,3-butanediol, 1,4-butanediol, 1,5-pentanediol, pentaerythritol, and sorbitol.

7. The method according to claim 1, wherein the step (3) and step (4) are omitted, and step (2) yields a liquid slurry of the stannous pyrophosphate product precipitate in the water or water/alcohol solvent mixture and this slurry is transferred into the mixing tank of step (5).

8. The method according to claim 1, wherein step (4) is omitted, and the filtered solid from step (3) is transferred into the mixing tank of step (5).

9. The method according to claim 1, wherein the reaction step (1) is substantially complete.

10. The method according to claim 1, wherein the method further comprises the step of incorporating stannous fluoride into the oral care composition.

11. A method of making stannous pyrophosphate, comprising the steps of (1) reacting stannous chloride with tetrasodium pyrophosphate in a water or water/alcohol solvent mixture, (2) precipitating the stannous pyrophosphate product, (3) recovering the stannous pyrophosphate product by filtration, and (4) freeze-drying the stannous pyrophosphate product.

12. The method of claim 11, wherein the stannous chloride is stannous chloride dihydrate ($SnCl_2 \cdot 2H_2O$).

13. The method according to claim 11, wherein the stannous chloride and the tetrasodium pyrophosphate are combined in a molar ratio of 1:1 to 1:3.

14. The method according to claim 11, wherein solvent for step (1) is water.

15. The method according to claim 11, wherein the solvent for step (1) is a water/alcohol mixture.

16. The method according to claim 15, wherein the alcohol is selected from methanol, ethanol, propanol, isopropanol, butanol, ethylene glycol, 1,2-propylene glycol, 1,3-propylene glycol, cyclopentane-1,2-diol, cyclohexane-1,2-diol, neopentyl glycol, glycerol, 1,2-butanediol, 1,3-butanediol, 1,4-butanediol, 1,5-pentanediol, pentaerythritol, and sorbitol.

17. An oral care composition comprising stannous pyrophosphate made according to the method of claim 11.

18. An oral care composition comprising stannous pyrophosphate and sodium chloride in a molar ratio of about 4 parts sodium chloride to one-part stannous pyrophosphate.

19. An oral care composition according to claim 18, wherein the composition comprises from 0.1 to 3% by weight of stannous pyrophosphate.

20. An oral care composition according to claim 18, wherein the composition comprises 0.05 to 2% by weight of sodium chloride.

* * * * *

UNITED STATES PATENT AND TRADEMARK OFFICE
CERTIFICATE OF CORRECTION

PATENT NO. : 11,110,042 B2
APPLICATION NO. : 16/820909
DATED : September 7, 2021
INVENTOR(S) : Zhigang Hao et al.

Page 1 of 1

It is certified that error appears in the above-identified patent and that said Letters Patent is hereby corrected as shown below:

In the Claims

In Column 10, Line 55, in Claim 9, delete "complete." and insert -- complete in 0-3 hours. --, therefor.

Signed and Sealed this
Eleventh Day of January, 2022

Drew Hirshfeld
*Performing the Functions and Duties of the*
*Under Secretary of Commerce for Intellectual Property and*
*Director of the United States Patent and Trademark Office*